 United States Patent
Cullis et al.

(12) United States Patent
Cullis et al.

(10) Patent No.: US 9,357,763 B2
(45) Date of Patent: Jun. 7, 2016

(54) CRYOPRESERVATION CONTAINER

(71) Applicant: Saint-Gobain Performance Plastics Corporation, Solon, OH (US)

(72) Inventors: Herbert Cullis, Gaithersburg, MD (US); Phillippe J. Broussard, Finksburg, MD (US)

(73) Assignee: Saint-Gobain Performance Plastics Corporation, Solon, OH (US)

( * ) Notice: Subject to any disclaimer, the term of this patent is extended or adjusted under 35 U.S.C. 154(b) by 36 days.

(21) Appl. No.: 14/493,855

(22) Filed: Sep. 23, 2014

(65) Prior Publication Data

US 2015/0087052 A1 Mar. 26, 2015

Related U.S. Application Data

(60) Provisional application No. 61/882,299, filed on Sep. 25, 2013.

(51) Int. Cl.
*A01N 1/00* (2006.01)
*A01N 1/02* (2006.01)

(52) U.S. Cl.
CPC ............... *A01N 1/00* (2013.01); *A01N 1/0263* (2013.01); *A01N 1/0268* (2013.01); *F25D 2700/00* (2013.01)

(58) Field of Classification Search
CPC .................................... A01N 1/00; B01L 3/50
USPC .......................................................... 422/40
See application file for complete search history.

(56) References Cited

U.S. PATENT DOCUMENTS

| 5,209,745 | A | 5/1993 | Irr et al. |
|---|---|---|---|
| 5,250,044 | A | 10/1993 | Irr et al. |
| 6,022,344 | A | 2/2000 | Meijer et al. |
| 8,028,532 | B2 | 10/2011 | Voute et al. |
| 8,177,123 | B2 | 5/2012 | Voute et al. |
| 8,313,821 | B2 | 11/2012 | Yan et al. |
| 8,336,734 | B2 | 12/2012 | Ware et al. |
| 8,449,520 | B2 | 5/2013 | Pepper et al. |
| 2002/0168759 | A1 | 11/2002 | Wang et al. |
| 2002/0177119 | A1 | 11/2002 | Wisniewski |
| 2004/0097862 | A1 | 5/2004 | Lampeter et al. |
| 2006/0246244 | A1 | 11/2006 | Jenkins et al. |
| 2007/0240432 | A1 | 10/2007 | Voute et al. |

(Continued)

OTHER PUBLICATIONS

International Search Report for Application No. PCT/US2014/056950, dated Jan. 2, 2015, 1 pg.

(Continued)

*Primary Examiner* — Sean E Conley
(74) *Attorney, Agent, or Firm* — Abel Law Group, LLP; Chi Suk Kim (57) ABSTRACT

A container includes an inner bag, where the interior of the inner bag includes a sterile environment for storing a material, at least one access port configured to provide fluid access to the interior of the inner bag, an overwrap bag, where the interior of the overwrap bag includes a sterile environment for storing the material and where the inner bag is enclosed within the interior of the overwrap bag, and an overwrap access port configured to provide fluid access to the interior of the overwrap bag. The material can include a biomaterial. Each of the inner bag, the overwrap bag, the at least one access port, and the overwrap access port can include a fluoropolymer such as fluoroethylenepropylene (FEP).

16 Claims, 4 Drawing Sheets

(56) References Cited

U.S. PATENT DOCUMENTS

| | | |
|---|---|---|
| 2008/0103428 A1 | 5/2008 | Delaronde-Wilton |
| 2008/0234654 A1 | 9/2008 | McCarthy et al. |
| 2009/0049845 A1 | 2/2009 | McStravick et al. |
| 2009/0107001 A1 | 4/2009 | McCarthy |
| 2009/0113753 A1 | 5/2009 | Pepper et al. |
| 2009/0158755 A1 | 6/2009 | Cutting et al. |
| 2009/0212071 A1 | 8/2009 | Tom et al. |
| 2009/0223080 A1 | 9/2009 | McCarthy et al. |
| 2009/0297769 A1 | 12/2009 | Yan et al. |
| 2010/0072216 A1 | 3/2010 | Voute et al. |
| 2010/0133292 A1 | 6/2010 | Ware et al. |
| 2011/0144613 A1 | 6/2011 | Pepper et al. |
| 2011/0247349 A1 | 10/2011 | Cutting et al. |
| 2012/0017609 A1 | 1/2012 | Voute et al. |

OTHER PUBLICATIONS

Khuu et al (2002), "Catastrophic failures of freezing bags for cellular therapy products: description, cause, and consequences". Cytotherapy vol. 4, No. 6, pp. 539-549.

CRYOPRESERVATION CONTAINER

CROSS-REFERENCE TO RELATED APPLICATION

The present application claims priority from U.S. Provisional Patent Application No. 61/882,299, filed Sep. 25, 2013, entitled "CRYOPRESERVATION CONTAINER," naming inventors Herbert Cullis and Philippe J. Broussard, which application is incorporated by reference herein in its entirety.

FIELD OF THE DISCLOSURE

The present disclosure relates to containers for the cryopreservation of material.

BACKGROUND

Container systems, such as those used to store and preserve critically important materials like biomaterials, can include plastics, metal cassettes, and glass containers. However, commercially available container systems are still prone to fracture during preservation processes, leading to potential leakage and loss of the material from the container as well as possible contamination of the material, the container, and the surrounding environment. Accordingly, a need continues to exist in the art for containers that can meet new and sometimes demanding applications, including for the sterile cryopreservation and storage of biomaterials.

SUMMARY

In an embodiment, a container includes an inner bag, where the interior of the inner bag includes a sterile environment for storing a material. The container includes at least one access port configured to provide fluid access to the interior of the inner bag. The container also includes an overwrap bag, where the interior of the overwrap bag includes a sterile environment for storing the material and where the inner bag is enclosed within the interior of the overwrap bag, and an overwrap access port configured to provide fluid access to the interior of the overwrap bag.

In another embodiment, a method of preserving a material, where the material includes a biomaterial, includes storing the material in a container, where the container includes an inner bag, and where the interior of the inner bag includes a sterile environment for storing a material. The container also includes at least one access port configured to provide fluid access to the interior of the inner bag. The container further includes an overwrap bag, where the interior of the overwrap bag includes a sterile environment for storing the material and where the inner bag is enclosed within the interior of the overwrap bag, and an overwrap access port is configured to provide fluid access to the interior of the overwrap bag.

In yet another embodiment, a container for cryopreserving a material in a sterile, closed environment, where the material includes a biomaterial, includes an inner bag, where the interior of the inner bag includes a sterile, closed environment for storing the material. The container also includes a spike port configured to provide fluid access to the interior of the inner bag and an inlet tube also configured to provide fluid access to the interior of the inner bag. The container further includes an overwrap bag, where the interior of the overwrap bag includes a sterile, closed environment for storing the material and where the inner bag is enclosed within the interior of the overwrap bag, and an overwrap access port including a spike port configured to provide fluid access to the interior of the overwrap bag. Each of the inner bag, the overwrap bag, the at least one access port, and the overwrap access port include fluoroethylenepropylene (FEP).

BRIEF DESCRIPTION OF THE DRAWINGS

Embodiments are illustrated by way of example and are not limited in the accompanying figures.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other teachings can certainly be used in this application.

Before addressing details of the embodiments described below, some terms and phrases are defined or clarified. The term "biomaterial" is intended to mean any suitable biological material including, for example, tissues, bone marrow, blood and blood products, cellular material or products, and microbial materials such as pathogens. The term "fluid access" is intended to encompass access to materials that have any combination of solid, liquid, and/or gaseous components.

The phrase "sterile environment" is intended to encompass an environment in which a material, such as a biomaterial, is preserved and/or stored without contamination, loss, or leakage of the material. The phrase "sterile environment" can encompass a "sterile, closed environment." The phrase "closed environment" includes an environment that is walled in or contained, in some instances completely. A "closed environment" also describes an environment that can communicate with or provide access to/from an outside environment, including another closed environment, but also may be configured to prevent communication with the outside environment or passage between the outside environment and the closed environment. For example, a closed environment may be able to communicate with an outside environment or another closed environment in some desired instances, but also may be configured in other instances to prevent exterior access to the other environment and/or interior access into the closed environment from the other environment. As such, a sterile, closed environment can include an environment that not only preserves and stores a material without contamination or loss of the material, but also is configured to allow or prevent the material from communicating with or passing to/from another environment (e.g., another closed environment) while protecting the material.

As used herein, the terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one or at least one and the singular also includes the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in reference books and other sources within the structural arts and corresponding manufacturing arts.

In an embodiment, the present invention provides for a container including an inner bag, where the interior of the inner bag includes a sterile environment for storing a material. The container includes at least one access port configured to provide fluid access to the interior of the inner bag. The container also includes an overwrap bag, where the interior of the overwrap bag includes a sterile environment for storing the material and where the inner bag is enclosed within the interior of the overwrap bag. The container further includes an overwrap access port configured to provide fluid access to the interior of the overwrap bag. A method of preserving a material, such as a biomaterial, is included in which a container as described herein is provided for storing the material.

The container as described herein is capable of storing material, including critically important biomaterials and any leak of those materials, in a sterile environment without risk of contamination to the material, the container, or an environment in which the container is placed. The container as described herein also is configured to provide a closed environment that prevents the stored material from communicating with or passing to/from an outside environment. As such, the container described herein is capable of providing a sterile, closed environment for the material. Components of the container (e.g., the inner bag and at least one access port sealed to it and/or the overwrap bag and an overwrap access port sealed to it) are also capable of providing additional sterile, closed environments for the material.

In an embodiment, the container is inert to the material stored inside of it. The container as described herein is better able to resist failure, such as fracture, during both preservation (e.g., cryopreservation) and thawing procedures as compared to commercially available containers. In an embodiment, the container is flexible and resistant to fracture over a range of temperatures from approximately ambient conditions, such as 20° C., 25° C., 30° C., or even 40° C., down to approximately −196° C., or the temperature of liquid nitrogen commonly used for cryopreservation processes.

The container includes an inner bag. The interior of the inner bag is sterile and therefore provides a sterile environment for the placement and storage of a material, including any suitable biomaterial. The interior of the inner bag can remain sterile in ambient conditions and in conditions used to preserve the material, including conditions consistent with cryopreservation procedures.

The inner bag can be made of any suitable material, including any material suitable for withstanding low temperature applications or cryopreservation processes. In an embodiment, the inner bag is made of at least one suitable polymeric material. For example, the inner bag can be made of a fluoropolymer, which may be formed of a homopolymer, copolymer, terpolymer, or polymer blend formed from a monomer, including tetrafluoroethylene, hexafluoropropylene, chlorotrifluoroethylene, trifluoroethylene, vinylidene fluoride, vinyl fluoride, perfluoropropyl vinyl ether, perfluoromethyl vinyl ether, or any combination thereof. Further, exemplary fluoropolymers include a fluorinated ethylene propylene copolymer (FEP), a copolymer including tetrafluoroethylene and perfluoropropyl vinyl ether (otherwise known as perfluoroalkoxy or PFA), a copolymer including tetrafluoroethylene and perfluoromethyl vinyl ether (MFA), a copolymer including ethylene and tetrafluoroethylene (ETFE), a copolymer including ethylene and chlorotrifluoroethylene (ECTFE), polychlorotrifluoroethylene (PCTFE), poly vinylidene fluoride (PVDF), a terpolymer including tetrafluoroethylene, hexafluoropropylene, and vinylidenefluoride (THV), or any blend or any alloy thereof. In a further example, the fluoropolymer may include a copolymer of tetrafluoroethylene and perfluoropropyl vinyl ether (perfluoroalkoxy or PFA). In an exemplary embodiment, the fluoropolymer may be a polymer crosslinkable through radiation, such as e-beam. An exemplary crosslinkable fluoropolymer may include ETFE, THV, PVDF, or any combination thereof. In an embodiment, the inner bag can include fluoroethylenepropylene (FEP). In a particular embodiment, the inner bag can consist essentially of FEP.

The inner bag may be formed from one piece of suitable material, or the inner bag may be formed from two or more pieces of suitable material that are seamed, welded, or otherwise adhered together. The inner bag can be formed from any suitable thickness of material, including a thickness of between about 0.05 millimeters (mm) and about 0.3 millimeters. The inner bag can be either opaque, transparent, or a combination thereof. In an embodiment, the inner bag is transparent to enable a user of the container to better visualize damage to the inner bag or a leak of the material.

The inner bag can include any suitable dimensions. In an embodiment, the inner bag can include a length between about 4 centimeters (cm) and about 40 centimeters. In a particular embodiment, the inner bag can include a length between about 15 and 21 centimeters. The inner bag also can include a width between about 2 centimeters and about 20 centimeters. The inner bag can include any suitable volume, including a volume configured to store any suitable volume of the material, such as a volume between about 0.1 milliliters (mL) and about 1,000 milliliters. In an embodiment, the inner bag can include a volume greater than 1,000 milliliters. The inner bag can further include any suitable polygonal shape, including a triangular, rectangular, or spherical shape.

The container includes at least one access port that is configured to provide or prevent fluid access to the interior of the inner bag. The at least one access port can be configured to place or transport material into the interior of the inner bag, remove or retrieve material from the inner bag, and any combination thereof. The inner bag in combination with the at least one access port sealed, welded, or otherwise affixed to the inner bag can be configured to provide a closed environment that prevents communication between the sterile environment of the inner bag and an outside environment, such as another closed environment. As such, the inner bag and the at least one access port sealed thereto can provide a sterile, closed environment for the material. In an embodiment, the container includes one access port configured to provide or prevent fluid access to the interior of the inner bag. In another embodiment, the container includes two or more access ports. In a particular embodiment, the container includes two access ports configured to provide or prevent fluid access to the interior of the inner bag. The access ports may be the same as or different from one another.

The at least one access port can be formed from any suitable material, including any material suitable for withstanding low temperature applications or cryopreservation processes. In an embodiment, the at least one access port is made of at least one suitable polymeric material. For example, the at least one access port can be made of a fluoropolymer, which may be formed of a homopolymer, copolymer, terpolymer, or polymer blend formed from a monomer, including tetrafluoroethylene, hexafluoropropylene, chlorotrifluoroethylene, trifluoroethylene, vinylidene fluoride, vinyl fluoride, perfluoropropyl vinyl ether, perfluoromethyl vinyl ether, or any combination thereof. Further, exemplary fluoropolymers include a fluorinated ethylene propylene copolymer (FEP), a copolymer including tetrafluoroethylene and perfluoropropyl vinyl ether (otherwise known as perfluoroalkoxy or PFA), a copolymer including tetrafluoroethylene and perfluoromethyl vinyl ether (MFA), a copolymer including ethylene and tetrafluoroethylene (ETFE), a copolymer including ethylene and chlorotrifluoroethylene (ECTFE), polychlorotrifluoroethylene (PCTFE), poly vinylidene fluoride (PVDF), a terpolymer including tetrafluoroethylene, hexafluoropropylene, and vinylidenefluoride (THV), or any blend or any alloy thereof. In a further example, the fluoropolymer may include a copolymer of tetrafluoroethylene and perfluoropropyl vinyl ether (perfluoroalkoxy or PFA). In an exemplary embodiment, the fluoropolymer may be a polymer crosslinkable through radiation, such as e-beam. An exemplary crosslinkable fluoropolymer may include ETFE, THV, PVDF, or any combination thereof. In an embodiment, the at least one access port can include polyvinylchloride (PVC), FEP, a thermoplastic elastomer (e.g., C-Flex®) or any combination thereof. In a particular embodiment, the at least one access port can consist essentially of FEP.

The at least one access port can be positioned in any suitable manner to provide fluid access to the interior of the inner bag. In an embodiment, the at least one access port can be positioned at least partially within the interior of the inner bag and at least partially outside of the interior of the inner bag. In a particular embodiment, the at least one access port can be at least partially positioned within a sealed cavity of the inner bag. The sealed cavity can be separated or partitioned from the interior of the inner bag by any suitable means, including by the use of one or more collar seals or welds. In another embodiment, the at least one access port can be positioned substantially within the interior of the inner bag. In yet another embodiment, the at least one access port can be enclosed by at least a portion of the inner bag, an overwrap bag, or a combination thereof such that the portion of the inner bag, the overwrap bag, or both covers the at least one access port. The cover formed by this portion of the inner bag, overwrap bag, or combination thereof, can be configured to expose or otherwise provide access to the least one access port by any suitable means, such as by tearing, cutting, or piercing the cover, or any combination thereof. Exposure of the at least one access port can provide evidence of tampering to a user of the container, consistent with specifications for sterile products.

The position of the at least one access port can be fixed (i.e., the at least one access port can be held in place) in any suitable manner. In an embodiment, the position of the at least one access port can be fixed with respect to the inner bag and its interior by means of a collar seal or a weld placed around at least a portion of the at least one access port. In another embodiment, the at least one access port can be hermetically sealed to the inner bag.

In addition to providing fluid access to the interior of the inner bag, the at least one access port can include any suitable exit port, any suitable inlet port, or any combination thereof. In a particular embodiment, fluid access can be provided to the interior of the inner bag through the at least one access port and the inner bag can include any suitable exit port, any suitable inlet port, or any combination thereof. The exit port can be configured for removing or retrieving material from the interior of the inner bag, or preventing the removal or retrieval thereof, including biomaterial that was stored or cryopreserved in the interior. The exit port can be configured to remove or retrieve that material in a sterile manner. The inlet port can be configured for placing or transporting material into the interior of the inner bag including biomaterial intended for storage or cryopreservation. The inlet port can be configured to place or transport the material into the interior in a sterile manner. In an embodiment, the container can include at least one inlet port and at least one exit port, both of which provide fluid access to the interior of the inner bag.

In an embodiment, the at least one access port can include any suitable exit port, such as a spike port. In a particular embodiment, the spike port can include any suitable membrane (e.g., septum), seal, or closure, which is configured to prevent leakage or removal of the material from the interior of the inner bag as part of a sterile environment as well as a closed environment. In an embodiment, the membrane can include any suitable thickness, such as a thickness of approximately 0.01 centimeters. The membrane or septum also can be used to provide evidence of tampering with the inner bag or the container. For example, the membrane or septum may be ruptured, pierced, or otherwise broken to remove or retrieve the material from the interior of the inner bag. A broken membrane can provide evidence to a user of the container that the stored material has been accessed and/or the sterility of the inner bag or the container has been compromised. Examples of commercially available spike ports include, for example, Pall #984-63, B. Braun #412113, Qosina #17601, #17605, #17606, #17607, #17608, #17609, and Saint-Gobain Gaithersburg #CS-186.

In another embodiment, the exit port includes any suitable luer activated device (LAD), the dimensions of which can be defined by, for example, ISO-594-1. In a particular embodiment, the exit port includes a luer valve such as a female luer valve. The luer valve can include any suitable closure means, such as an internal valve, configured to prevent leakage or removal of the material from the interior of the inner bag as part of a sterile environment as well as a closed environment. The internal valve can include any suitable material, such as an elastomer (e.g., rubber). The luer valve further includes a female luer end and a male luer fitting or end. The internal valve is configured to open, for example by having sides that move apart, when a male luer fitting is attached to the female luer end, thereby providing fluid access to the interior of the inner bag. The internal valve is configured to close, thereby preventing fluid access and preventing a leak of the material from the interior of the inner bag, when the male luer fitting is detached from the female luer end.

In an embodiment, the at least one access port can be configured as an inlet port. In a particular embodiment, the inlet port can include an inlet tube. The inlet tube can include any suitable material, including a material that is capable of being sealed or otherwise closed using a variety of techniques such as pinching, heat sealing, welding, dielectric sealing, radio-frequency welding, ultrasonic welding, or any combination thereof. For example, the inlet tube can include biologically compatible polymeric materials such as PVC, FEP, a thermoplastic elastomer such as C-Flex®, or any combination thereof. In an embodiment, the inlet tube can include material or materials that are the same as, or different from, the material or materials used in another access port or ports in the container. In a particular embodiment, the inlet tube can include intravenous tubing.

The inlet tube also can include any suitable dimensions, including any suitable dimensions for connecting to an external source, such as for sterile docking purposes, and transporting the material (e.g., a biomaterial). In an embodiment, the inlet tube can include any suitable length positioned outside of an overwrap bag of the container, such as a length between about 10 centimeters and 20 centimeters. The diameter of the inlet tube can include any suitable diameter, such as at least 1 millimeter (mm), at least 2 mm, at least 3 mm, at least 4 mm, or even at least 5 mm. In a particular embodiment, the inlet tubing can include an internal diameter of approximately 3 mm and an external diameter of approximately 4 mm.

In an embodiment, the inlet tube can include any suitable number of tubing pieces or components. For example, the inlet tube can include one piece of a polymeric material such as PVC, FEP, or C-Flex®. In another embodiment, the inlet tube can include two or more pieces held together by any suitable means (e.g., a bushing), and can include more than one polymeric material, such as a combination of two or more of PVC, FEP, and C-Flex®.

An inlet port, such as the inlet tube, can be configured to connect to an external source for placing or transporting the material into the inner bag in a sterile manner. The external source can include any suitable vessel, container, or system for maintaining a material like a biomaterial in a sterile environment. The inlet tube can be heated, spliced, or otherwise connected to the external source in any suitable manner, such as through a sterile docking or hot knife technique. The connection between the inlet tube and the external source can establish a sterile pathway for transportation of the material into the interior of the inner bag.

The inlet tube is configured to close after the material has been transported into the inner bag to create a closed environment for the material within the inner bag. In an embodiment, the inlet tube can be sealed in one or more places, such as two places, three places, or even four places, including at a place immediately exterior to an overwrap bag, to prevent leakage of the material from the interior of the inner bag and contamination of the material, the inner bag, or the container. For example, the inlet tube can include at least one piece of PVC tubing that can be heated or melted shut to form at least one seal in one or more places along the length of the inlet tube. In another embodiment, the inlet tube can be closed using a mechanical force, such as metallic jaws, plates, or surfaces that press the inlet tube closed. After the inlet tube is closed, the inlet tube is configured to disconnect, in a sterile manner and by any suitable means, from the external source. In an embodiment, a portion of the sealed or closed inlet tube can be separated from another portion of the inlet tube using, for example, scissors.

Although the luer valve and the spike port have been described herein as exit ports for removing material from the interior of the inner bag, it will be appreciated that each of the luer valve and spike port also can be configured as inlet ports for placing or transporting material into the interior of the inner bag. Similarly, although the inlet tube has been described herein as an inlet port for transporting material into the inner bag, it will be appreciated that the inlet tube also can be configured as an exit port for removing material from the interior of the inner bag.

The container further includes an overwrap bag. Like the inner bag, the interior of the overwrap bag is sterile and therefore provides a sterile environment for the containment and storage of a material, including any suitable biomaterial. In addition, the interior of the overwrap bag can remain sterile both in ambient conditions and in conditions used to preserve the material, including conditions consistent with cryopreservation procedures. Furthermore, the inner bag is enclosed within the interior of the overwrap bag. In a particular embodiment, the overwrap bag is configured to store a leak of the material from the interior of the inner bag within the interior of the overwrap bag.

The overwrap bag can be formed from any suitable material, including any material suitable for withstanding low temperature applications or cryopreservation processes. In an embodiment, the overwrap bag is made of at least one suitable polymeric material. For example, the overwrap bag can be made of a fluoropolymer, which may be formed of a homopolymer, copolymer, terpolymer, or polymer blend formed from a monomer, including tetrafluoroethylene, hexafluoropropylene, chlorotrifluoroethylene, trifluoroethylene, vinylidene fluoride, vinyl fluoride, perfluoropropyl vinyl ether, perfluoromethyl vinyl ether, or any combination thereof. Further, exemplary fluoropolymers include a fluorinated ethylene propylene copolymer (FEP), a copolymer including tetrafluoroethylene and perfluoropropyl vinyl ether (otherwise known as perfluoroalkoxy or PFA), a copolymer including tetrafluoroethylene and perfluoromethyl vinyl ether (MFA), a copolymer of ethylene and tetrafluoroethylene (ETFE), a copolymer including ethylene and chlorotrifluoroethylene (ECTFE), polychlorotrifluoroethylene (PCTFE), poly vinylidene fluoride (PVDF), a terpolymer including tetrafluoroethylene, hexafluoropropylene, and vinylidenefluoride (THV), or any blend or any alloy thereof. In a further example, the fluoropolymer may include a copolymer of tetrafluoroethylene and perfluoropropyl vinyl ether (perfluoroalkoxy or PFA). In an exemplary embodiment, the fluoropolymer may be a polymer crosslinkable through radiation, such as e-beam. An exemplary crosslinkable fluoropolymer may include ETFE, THV, PVDF, or any combination thereof. For instance, the overwrap bag can include FEP and, in an embodiment, can consist essentially of FEP. In another embodiment, the overwrap bag can include the same material as, or a different material from, the inner bag.

The overwrap bag may be formed from one piece of suitable material or may be formed from two or more pieces of suitable material. The overwrap bag also can be formed from any suitable thickness of material, including a thickness of between about 0.05 millimeters and about 0.3 millimeters. The overwrap bag can be either opaque, transparent, or a combination thereof. In an embodiment, the overwrap bag is transparent to enable a user of the container to better visualize damage to the overwrap bag or a leak of the material.

The overwrap bag can include any suitable dimensions. In an embodiment, the overwrap bag can include a length between about 6 centimeters and about 60 centimeters. In a particular embodiment, the overwrap bag can include a length between about 22 and 28 centimeters. The overwrap bag also can include a width between about 5 centimeters and about 50 centimeters. The overwrap bag can include any suitable volume, including a volume between about 0.1 milliliters (mL) and about 2,000 milliliters, where the volume of the overwrap bag is sufficient to accommodate the enclosure of the inner bag and the material within the interior of the overwrap bag. In an embodiment, the volume of the overwrap bag is greater than the volume of the inner bag. In another embodiment, the overwrap bag can include a volume of greater than 2,000 milliliters. The interior of the overwrap bag also can store a leak of the material, including a volume of material between about 0.1 milliliters and about 2,000 milliliters, or a volume greater than about 2,000 milliliters. The overwrap bag can further include any suitable polygonal shape, including a triangular, rectangular, or spherical shape.

The container also includes an overwrap access port that is configured to provide or prevent fluid access to the interior of the overwrap bag. Like the at least one access port that is configured to provide or prevent fluid access to the interior of the inner bag, the overwrap access port can be configured to place or transport material into the interior of the overwrap bag as an inlet port, remove or retrieve material from the overwrap bag as an exit port, and any combination thereof. The overwrap bag in combination with the overwrap access port sealed, welded, or otherwise affixed to the overwrap bag can be configured to provide a closed environment that prevents communication between the sterile environment of the overwrap bag and an outside environment, such as another closed environment. As such, the overwrap bag and the overwrap access port sealed thereto can provide a sterile, closed environment for the material. In an embodiment, the container includes one overwrap access port configured to provide or prevent fluid access to the interior of the overwrap bag. In another embodiment, the container includes two or more overwrap access ports. In a particular embodiment, the at least one access port associated with the inner bag can be the same as, or different from, the overwrap access port. For example, the overwrap access port can include a spike port or a luer valve as described above.

The overwrap access port can be formed from any suitable material, including the same material as, or a different material from, the at least one access port and including any material suitable for withstanding low temperature applications or cryopreservation processes. In an embodiment, the overwrap access port is made of at least one suitable polymeric material. For example, the overwrap access port can be made of a fluoropolymer, which may be formed of a homopolymer, copolymer, terpolymer, or polymer blend formed from a monomer, including tetrafluoroethylene, hexafluoropropylene, chlorotrifluoroethylene, trifluoroethylene, vinylidene fluoride, vinyl fluoride, perfluoropropyl vinyl ether, perfluoromethyl vinyl ether, or any combination thereof. Further, exemplary fluoropolymers include a fluorinated ethylene propylene copolymer (FEP), a copolymer including tetrafluoroethylene and perfluoropropyl vinyl ether (otherwise known as perfluoroalkoxy or PFA), a copolymer including tetrafluoroethylene and perfluoromethyl vinyl ether (MFA), a copolymer including ethylene and tetrafluoroethylene (ETFE), a copolymer including ethylene and chlorotrifluoroethylene (ECTFE), polychlorotrifluoroethylene (PCTFE), poly vinylidene fluoride (PVDF), a terpolymer including tetrafluoroethylene, hexafluoropropylene, and vinylidenefluoride (THV), or any blend or any alloy thereof. In a further example, the fluoropolymer may include a copolymer of tetrafluoroethylene and perfluoropropyl vinyl ether (perfluoroalkoxy or PFA). In an exemplary embodiment, the fluoropolymer may be a polymer crosslinkable through radiation, such as e-beam. An exemplary crosslinkable fluoropolymer may include ETFE, THV, PVDF, or any combination thereof. For instance, the overwrap access port can include FEP. In an embodiment, the overwrap access port can consist essentially of FEP.

The overwrap access port can be positioned in any suitable manner to provide or prevent fluid access to the interior of the overwrap bag. In an embodiment, the overwrap access port can be positioned at least partially within the interior of the overwrap bag and at least partially outside of the interior of the overwrap bag. In another embodiment, the overwrap access port can be positioned substantially within the interior of the overwrap bag. In yet another embodiment, the overwrap access port can be enclosed within the overwrap bag such that at least a portion of the overwrap bag covers the overwrap access port. The cover (e.g., a secondary cover) formed by this portion of the overwrap bag can be configured to expose or otherwise provide access to the overwrap access port by any suitable means, such as by tearing, cutting, or piercing the secondary cover, or any combination thereof. Exposure of the overwrap access port can provide evidence of tampering to a user of the container, consistent with specifications for sterile products.

The position of the overwrap access port can be fixed (i.e., the overwrap access port can be held in place) in any suitable manner. In an embodiment, the position of the overwrap access port is fixed with respect to the overwrap bag and its interior by means of a collar seal or a weld placed around at least a portion of the overwrap access port. In another embodiment, the overwrap access port can be hermetically sealed to the overwrap bag.

The at least one access port of the inner bag, which can include a spike port, a luer valve, and/or an inlet tube as described above, also can be configured in a variety of positions relative to the overwrap bag. In an embodiment, the at least one access port can be positioned at least partially within the interior of the overwrap bag and at least partially outside of the interior of the overwrap bag (e.g., at least partially exterior to the container). In another embodiment, the at least one access port can be positioned substantially within the interior of the overwrap bag. In yet another embodiment, the at least one access port can be at least partially enclosed within the overwrap bag such that at least a portion of the overwrap bag (e.g., a cover) covers the at least one access port.

In some embodiments, the overwrap bag can include an integral label pocket configured to store a label. The pocket can include any suitable dimensions to accommodate the label, including a width commensurate with the width of the overwrap bag and a length between about 5 centimeters (cm) and about 50 centimeters, such as between about 7 and 13 centimeters long. The label can include any suitable information, such as identifying information about a patient and their medical history, the contents of the material in the container, and the date on which the material was obtained and/or stored in the container. Including such a label inside the label pocket also satisfies various regulatory requirements to label unambiguously the container so as to prevent misidentification of containers at a storage facility.

To prevent loss of the label, the label pocket is configured to close once the label is placed inside the label pocket. The label pocket can be closed in any suitable manner, including by pinching, heat sealing, welding, dielectric sealing, radio-frequency welding, ultrasonic welding, stapling, taping, or any combination thereof. Closing the label pocket can also protect the label from damage while the container is being used or stored. For example, the label pocket can protect the label from smudging, defacing, tearing, deterioration, or any combination thereof.

The container can be filled with a material to be stored or preserved (e.g., frozen) in any suitable manner. The material can be introduced in a sterile manner into the interior of the inner bag by an external source connected to the at least one access port. In an embodiment, the material is transported in a sterile manner into the interior of the inner bag via a sterile docking technique and an inlet tube as described above. After the material has been transported in a sterile manner from the external source to the interior of the inner bag, the external source and/or the at least one access port can be sealed or otherwise closed off to provide a closed environment for the material and to prevent leakage of the material from the container and contamination of the material, the container, and the surrounding environment. The external source and/or the at least one access port can be closed in any suitable manner, including by pinching, heat sealing, welding, dielectric sealing, radio-frequency welding, ultrasonic welding, or any combination thereof. In a particular embodiment, an inlet tube can be closed or heat sealed in more than one place, including in a location outside of the overwrap bag and in at least one location within the sealed cavity, using a thermal or radio frequency heated jaw to melt the inlet tube closed. In another embodiment, the inlet tube can be sealed within the sealed cavity without damage to the overwrap bag because the overwrap bag may include a material that has a high melt temperature and/or immunity to radio frequency melting. In another embodiment, the inlet tube could be pinched closed by means of mechanical force. The external source then can be detached from the at least one access port in a sterile manner. For example, the inlet tube can be cut through a seal that is located outside of the overwrap bag so as to separate the inlet tube from the external source. In an embodiment, after the at least one access port has been closed, at least a portion of the inner bag, the overwrap bag, or a combination thereof, also can be used to cover over or seal the at least one access port. Covering the at least one access port with a portion of the inner bag, the overwrap bag, or both, can help prevent leaks of the material or contamination of the material, the container, or the surrounding environment if the at least one access port were to fracture or break during storage.

The container can then be frozen by any suitable method for any suitable period of time. In an embodiment, the container can be dunked into a bath or vessel containing liquid nitrogen. In another embodiment, the container can be subjected to controlled rate freezing or another method of stepwise freezing. For example, the container can be placed between two surfaces that can cool the container at any suitable rate between approximately 0.1° C. per minute and 10° C. per minute, such as at a rate of 1° C. per minute. After the container and the material are frozen, the container can be placed into frozen storage, such as a cryopreservation system.

The container can be emptied of the material and the material can be accessed in any suitable manner. In an embodiment, the container can be removed from frozen storage and the container and material can be thawed in any suitable manner. For example, the container can be placed into a warm water bath between approximately 20° C. and 40° C. for either rapid or gradual thawing. After thawing is complete, the container can be visually inspected to determine if any of the material has leaked from the interior of the inner bag into the interior of the overwrap bag. If a leak has occurred, the overwrap access port can be exposed and the material in the interior of the overwrap bag can be accessed through the overwrap access port. Any material still contained within the interior of the inner bag, regardless of whether a leak has occurred, can be accessed by exposing the at least one access port and accessing the material through the at least one access port. In an embodiment, at least one of the overwrap access port and the at least one access port can include a spike port and the material can be accessed by piercing the membrane of the spike port with, for example, a spike or a syringe.

Figure 1:
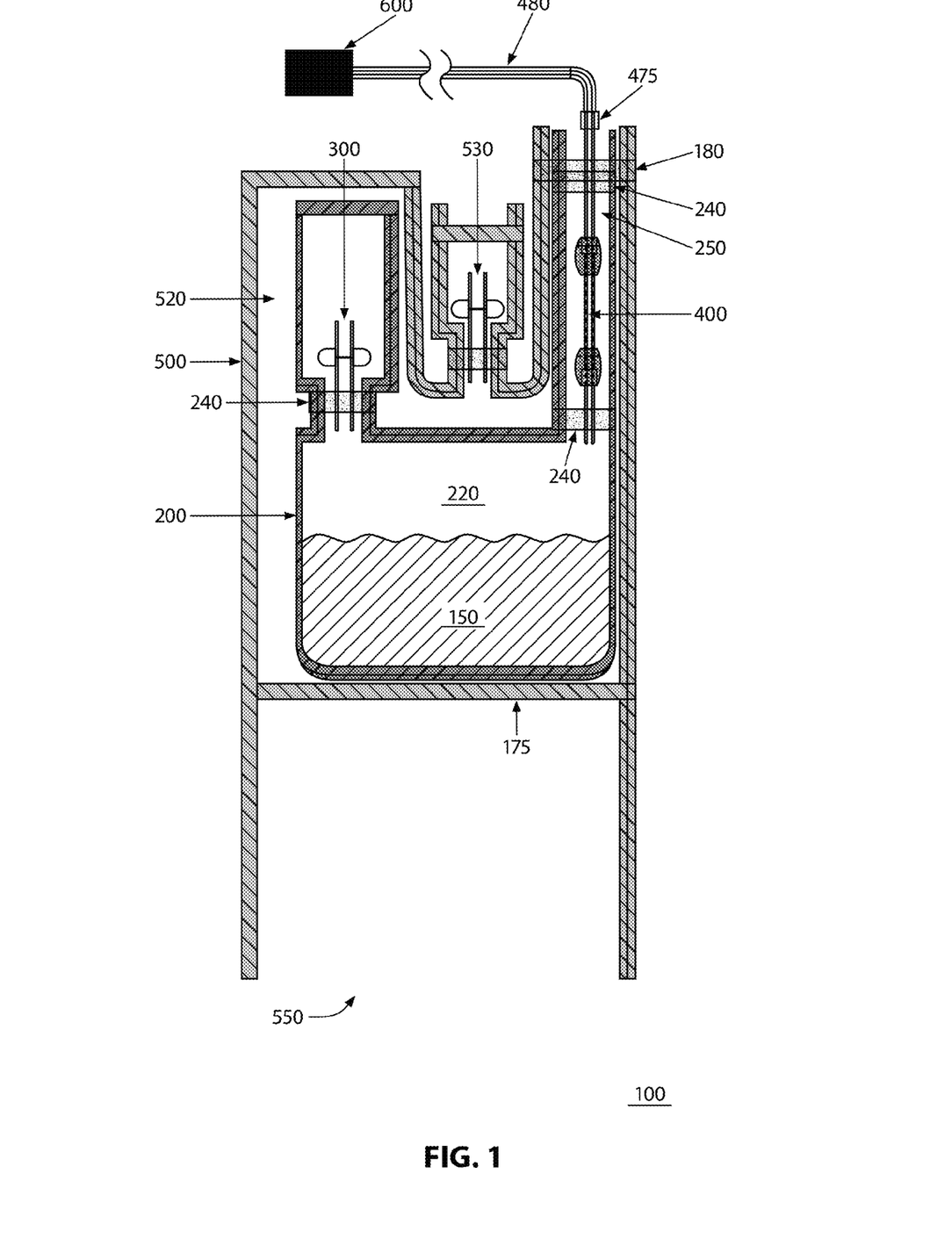
FIG. 1 depicts a container illustrated in accordance with an embodiment described herein.

Turning to FIG. 1, a container 100 is illustrated in accordance with an embodiment described herein. The container 100 is suitable for the cryopreservation of a material 150, including a biomaterial such as bone marrow. The container 100 includes an inner bag 200 with an interior 220 that includes a sterile environment for storing the material 150. In conjunction with at least one access port sealed or affixed thereto, the inner bag 200 also provides a closed environment for the material 150. In particular, the container 100 includes two access ports, namely an exit port (e.g., spike port 300) and an inlet port (e.g., inlet tube 400), which are configured to provide or prevent fluid access to the interior 220 of the inner bag 200. The inlet tube 400 is at least partially enclosed within a sealed cavity 250. In an embodiment, at least one of the spike port 300 and the inlet tube 400 may be sealed to the inner bag 200 by means of a seal, such as a seal 240, and the inlet tube 400 also may be sealed to an overwrap bag 500 by means of a seal, such as a seal 180. In a particular embodiment, the seals 240 and/or 180 may completely surround a portion of the spike port 300 and/or the inlet tube 400. As such, the inner bag 200 in conjunction with the spike port 300 and/or the inlet tube 400 being sealed to the inner bag 200 creates a closed environment for the material 150.

The inlet tube 400 is configured to connect in a sterile manner, such as through a sterile docking technique, to an external source 600 that maintains the material 150 in a sterile environment. After the material 150 has been transported in a sterile manner (e.g., along a sterile pathway 480) from the external source 600 to the interior 220 of the inner bag 200, the inlet tube 400 is closed in a suitable manner, including by means of a collar seal 475 and additional seals (not shown), to provide a closed environment and to prevent leakage of the material 150 from the container 100 and contamination of the inner bag 200 or the container 100. The inlet tube 400 then is detached (not shown) from the external source 600. In an embodiment, a portion (not shown) of an overwrap bag 500 also can extend along an exterior portion of the inlet tube 400 and can be sealed over the inlet tube 400. The inlet tube 400 can be sealed to either or both of the overwrap bag 500 (e.g., by the seal 180) and the inner bag 200 (e.g., by the seal 240). In another embodiment, the inlet tube 400 also can be cut above the collar seal 475 (not shown) to further detach the inlet tube 400 from the external source 600.

The container 100 also includes an overwrap bag 500. The interior 520 of the overwrap bag 500 includes a sterile environment for storing the material 150. The inner bag 200 is enclosed within the interior 520 of the overwrap bag 500. The container 100 further includes at least one overwrap access port 530 that is configured to provide or prevent fluid access to the interior 520 of the overwrap bag 500. Such fluid access enables a user of the container 100 to retrieve material 150 if, for example, a leak of the material 150 is contained within the interior 520. In conjunction with the overwrap access port 530 sealed or affixed thereto, the overwrap bag 500 also provides a closed environment for the material 150. The overwrap bag 500 also includes the seals 175 and 180 that serve to enclose the inner bag 200 and to create a label pocket 550 for storing a label that includes appropriate identifying information. After a label is placed in the label pocket 550, the label pocket 550 can be closed (not shown) to protect the label during subsequent cryopreservation processes. In an embodiment, the inner bag 200 may be placed into the overwrap bag 500 during a manufacturing process in which an appendix or portion 570 (FIG. 5) that is used to maintain the sterility of the overwrap bag 500 is permanently removed from the overwrap bag 500, but before the seal 175 is added. The inner bag 200 may be sealed within the overwrap bag by means of the seal 175 and sealed to the overwrap bag by means of the seal 180. The seal 180 may take the place of the portion 570 in maintaining the sterility of the overwrap bag 500 and may contribute to each of the container 100, the inner bag 200, and the overwrap bag 500 providing closed environments for the material 150.

Figure 2:
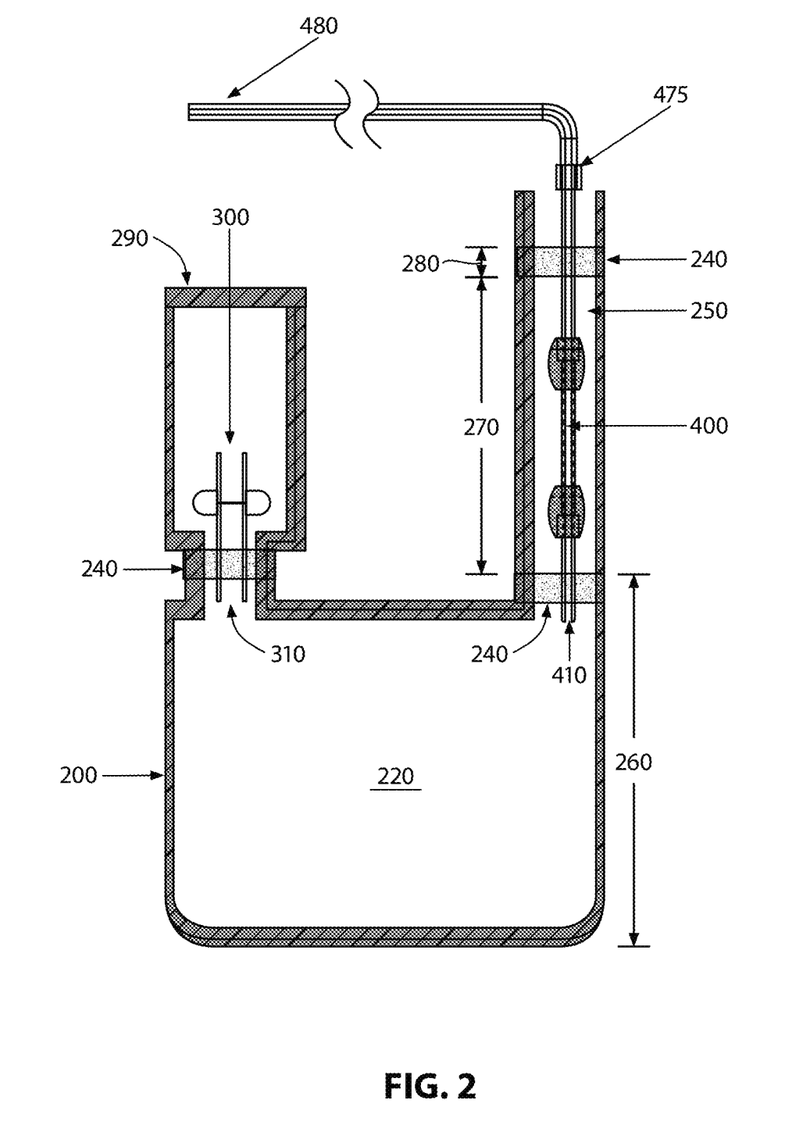
FIG. 2 depicts an inner bag and access ports illustrated in accordance with an embodiment described herein.

Turning to FIG. 2, the inner bag 200 and access ports 300 and 400 are illustrated in accordance with an embodiment described herein. The interior 220 of the inner bag can include any suitable dimensions, including a height 260 between approximately 4 centimeters and 40 centimeters, such as a height of about 9.9 centimeters. The sealed cavity 250 also can include any suitable dimensions, including a height 270 between approximately 2 centimeters and 20 centimeters, such as a height of about 7.6 centimeters. In an embodiment, the inner bag 200 and access ports 300 and 400 sealed thereto can include a closed environment for a material. For example, the closed environment can contain a material within the interior 220 of the inner bag 200 and prevent it from escaping through either of the access ports 300 or 400 sealed to the inner bag 200 (i.e. because a membrane in the access port 300 is intact or because the access port 400 is sealed or otherwise closed off at least once from an outside environment).

One access port, namely the spike port 300, can be positioned such that an end 310 is positioned at least partially within the interior 220 of the inner bag 200, thereby enabling a user of the container 100 to access the material 150 in the interior 220 through the spike port 300. The spike port 300 can be fixed in position relative to the inner bag 200 by any suitable means, including by means of a weld 240. The spike port 300 also can be at least partially covered by a portion of the inner bag 200, such as by a cover 290. To expose the spike port 300 and access the material 150 (not shown), the cover 290 can be torn, cut, pierced, or otherwise broken.

Another access port, namely the inlet tube 400, can be positioned such that an end 410 is positioned at least partially within the interior 220 of the inner bag 200, thereby enabling a user of the container 100 to transport the material 150 into the interior 220 through the inlet tube 400. The inlet tube 400 can be fixed in position within the sealed cavity 250 and relative to the inner bag 200 by any suitable means, including by means of the welds 240. In an embodiment, the weld 240 includes a thickness 280 of approximately 0.75 centimeters. The welds 240 also serve to separate the sealed cavity 250 from the interior 220 of the inner bag 200, further isolating the material 150 from possible leakage or contamination.

Figure 3A:
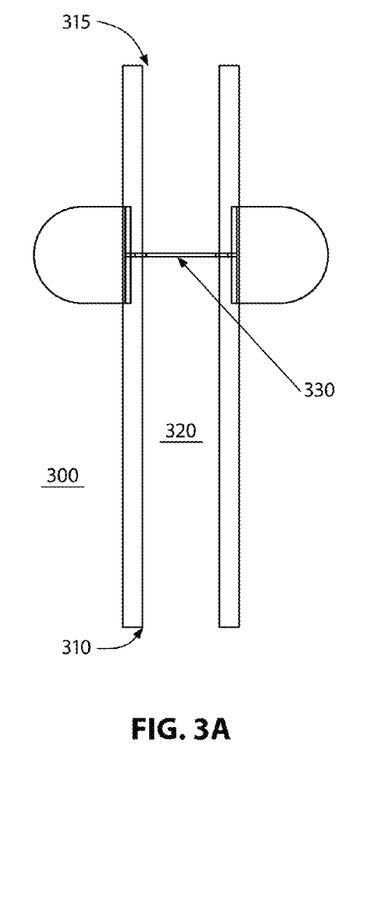
FIG. 3A depicts a spike port illustrated in accordance with an embodiment described herein.

Turning to FIG. 3A, the spike port 300 is illustrated in accordance with an embodiment described herein. The spike port 300 includes ends 310 and 315 and a lumen or pathway 320. The spike port 300 also includes membrane 330. Ends 310 and 315 are prevented from being in fluid communication with one another, and fluid access is prevented through the spike port 300, when membrane 330 is intact. When membrane 330 is pierced, penetrated, or otherwise broken, the lumen 320 permits fluid communication between ends 310 and 315 and fluid access can occur through the spike port 300. The membrane 330 can be pierced by any suitable means to establish fluid access, including a spike or syringe.

Figure 3B:
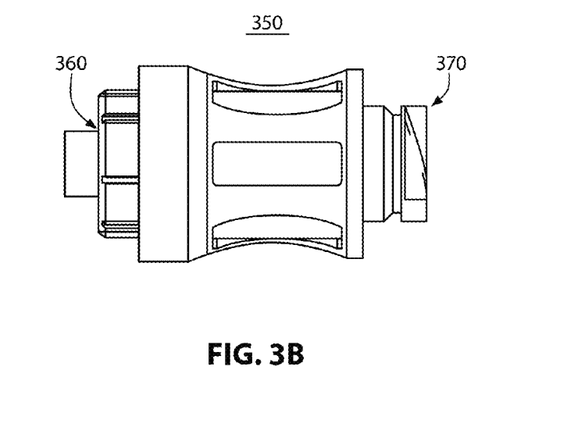
FIG. 3B depicts a luer valve illustrated in accordance with an embodiment described herein.

Turning to FIG. 3B, a luer valve 350 is illustrated in accordance with an embodiment described herein. As an alternative to, or in addition to, the spike port 300 or 530, the luer valve 350 can be used with the container 100 to provide fluid access to either of the inner bag 200 or the overwrap bag 500. The luer valve 350 includes a male luer fitting 360 and a female luer end 370, both of which can be threaded. In an embodiment, at least one end of the luer valve 350, such as the male luer fitting 360, is positioned at least partially within the interior of either the inner bag 200 or the overwrap bag 500. The female luer end 370 can be positioned to face out of and away from the interior of the inner bag 200 or the overwrap bag 500. The luer valve 350 also includes an internal valve (not shown). The internal valve is configured to open to provide fluid access to the interior of either of the inner bag 200 or the overwrap bag 500 when, for example, another male luer fitting (not shown) is attached to the female luer end 370. An example of the other male luer fitting can include a syringe. The internal valve is configured to close, thereby preventing fluid access to and leakage of the material 150 from the interior of either bag, when the other male luer fitting is detached thereafter from the female luer end 370.

Figure 4:
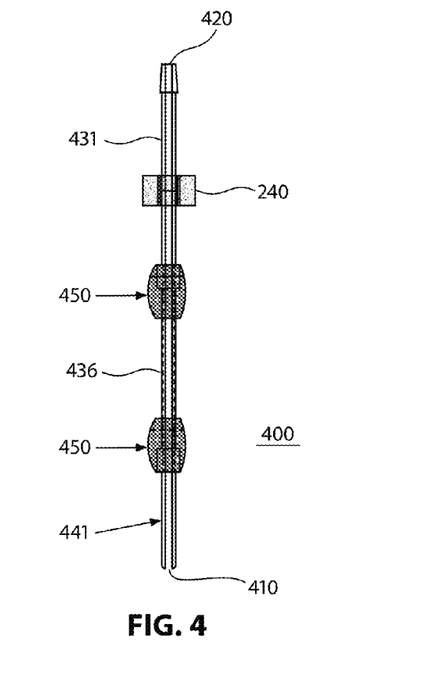
FIG. 4 depicts an inlet tube illustrated in accordance with an embodiment described herein.

Turning to FIG. 4, the inlet tube 400 is illustrated in accordance with an embodiment described herein. The inlet tube 400 includes an open end 410 positioned at least partially within the interior 220 of the inner bag 200 as described above. The inlet tube also includes an end 420 that can be configured for sealing or closing (e.g., by means described above) to prevent leaks from or contamination of the container 100. In an embodiment, the end 420 can include a material suitable for sealing, such as PVC. In addition, the end 420 can be configured for connection to a male luer fitting 360, which thereafter can be connected to a female luer end 370 to form a closed pathway. It will be understood that, in an embodiment, the end 420 either can be connected to a male luer fitting 360 or otherwise can be sealed off; the end 420 is not left open in practice.

The inlet tube 400 can include any suitable number of tubing pieces or components. For example, the inlet tube can include pieces 431, 436, and 441. The pieces 431, 436, and 441 can include the same or different materials, including any suitable biologically compatible materials like PVC, FEP, and/or C-Flex®. In an embodiment, the piece 431 can be suitable for sealing and can be positioned at least partially exterior to the overwrap bag 500. The piece 431 can be connected to a bushing 450. For example, the piece 431 can be hermetically sealed to the bushing 450, which can include FEP. The piece 436 can connect the bushings 450, and in an embodiment, the piece 436 can include PVC, making it capable of also being sealed in at least one place (not shown) by any suitable means. The piece 441 also can be hermetically sealed to the bushing 450. In an embodiment, the piece 441 can be positioned at least partially within the interior 220 of the inner bag 200 so as to complete a fluid path from the outside of the overwrap bag 500 through the sealed cavity 250 to the interior 220 of the inner bag 200. In a particular embodiment, the piece 441 can include FEP.

Figure 5:
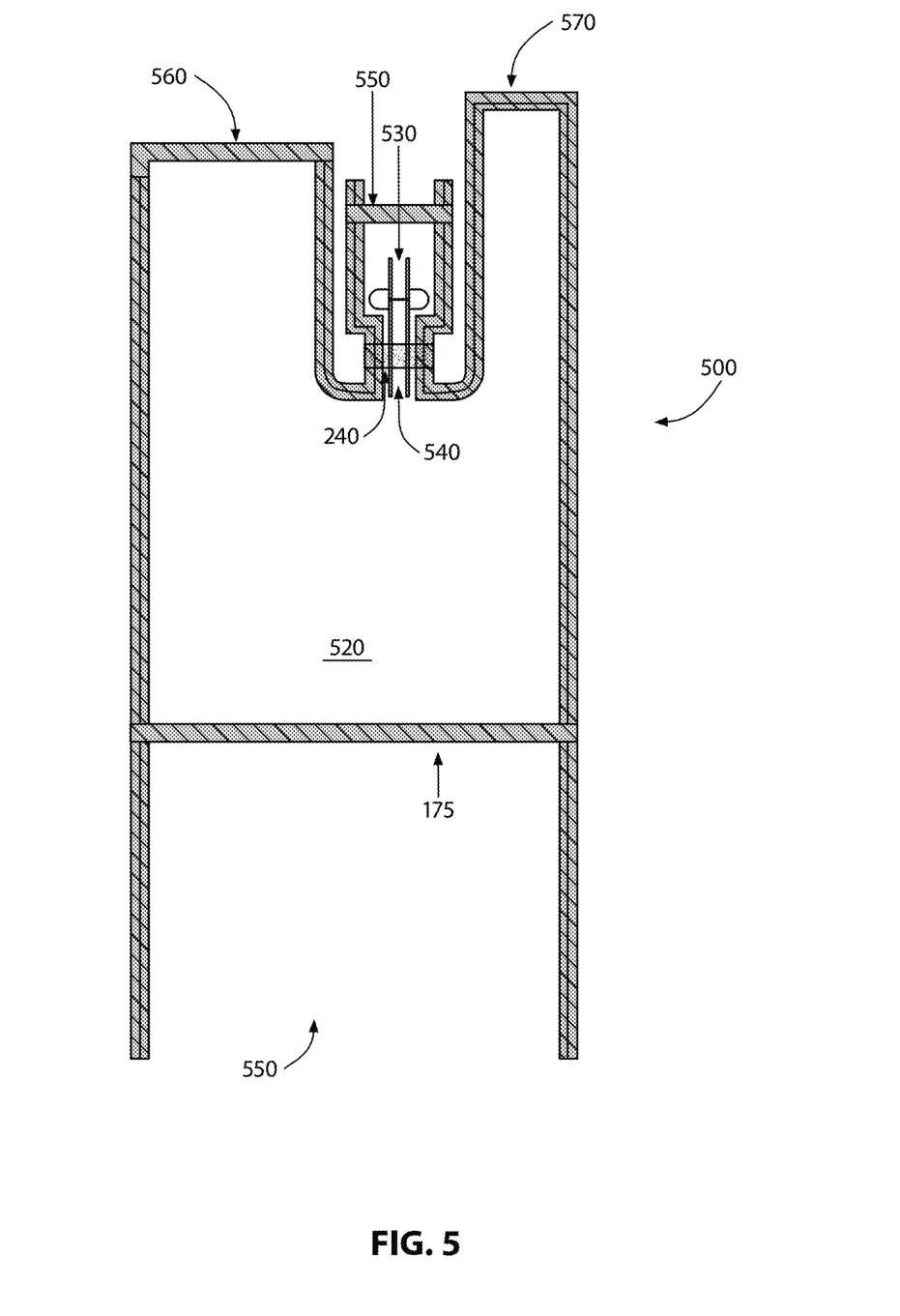
FIG. 5 depicts an overwrap bag and an overwrap access port illustrated in accordance with an embodiment described herein.

Turning to FIG. 5, the overwrap bag 500 with the overwrap access port 530 is illustrated in accordance with an embodiment described herein. The overwrap access port 530 includes an end 540 positioned at least partially within the sterile interior 520 of the overwrap bag so as to provide a user of the container 100 with fluid access to the interior 520. If a leak of the material 150 (not shown) results in at least some of the material 150 being contained within the interior 520, the material 150 can be accessed and removed from the interior 520 via the overwrap access port 530. In an embodiment, the overwrap access port 530 can include a spike port that is similar to the spike port 300, or can include a different type of port or valve. The position of the overwrap access port 530 relative to the overwrap bag 500 can be fixed by any suitable means, including a weld 240. The seal 240 may completely surround a portion of the overwrap access port 530. In an embodiment, the overwrap bag 500 and the overwrap access port 530 sealed thereto can include a closed environment for a material. For example, the closed environment can contain a material within the interior 520 of the overwrap bag 500 and prevent it from escaping through the overwrap access port 530 sealed to the overwrap bag 500 (i.e. because a membrane in the overwrap access port 530 is intact).

The overwrap access port can be at least partially covered by a portion of the overwrap bag 500, such as by a secondary cover 550. The secondary cover 550 serves to protect the overwrap access port 530 from contamination by an outside environment including, for example, a liquid nitrogen bath into which the container 100 is placed. To expose the overwrap bag port 530 and, in some instances, provide evidence that the container or the overwrap access port 530 has been tampered with, the secondary cover 550 can be torn, cut, pierced, or otherwise broken. In an embodiment, portions 560 and 570 of the overwrap bag 500 can also cover and/or be sealed to other parts of the container 100, such as the spike port 300 and the inlet tube 400, respectively. In a particular embodiment, the appendix or portion 570 that can be used to initially maintain the sterility of the overwrap bag 500, including the interior 520, also can be permanently removed from the overwrap bag 500 prior to insertion of the inner bag 200 within the overwrap bag 500 and sealing of the inner bag 200 to the overwrap bag via the seal 180.

Items

Item 1. A container including an inner bag, wherein the interior of the inner bag includes a sterile environment for storing a material; at least one access port configured to provide fluid access to the interior of the inner bag; an overwrap bag, wherein the interior of the overwrap bag includes a sterile environment for storing the material and wherein the inner bag is enclosed within the interior of the overwrap bag; and an overwrap access port configured to provide fluid access to the interior of the overwrap bag.

Item 2. The container of item 1, wherein the material includes a biomaterial, such as bone marrow.

Item 3. A method of preserving a material, wherein the material includes a biomaterial, the method including: storing the material in a container, wherein the container includes: an inner bag, wherein the interior of the inner bag includes a sterile environment for storing the material; at least one access port configured to provide fluid access to the interior of the inner bag; an overwrap bag, wherein the interior of the overwrap bag includes a sterile environment for storing the material and wherein the inner bag is enclosed within the interior of the overwrap bag; and an overwrap access port configured to provide fluid access to the interior of the overwrap bag.

Item 4. The container or the method of any one of the preceding items, wherein at least one of the inner bag, the overwrap bag, the at least one access port, and the overwrap access port includes a polymer, such as fluoroethylenepropylene (FEP).

Item 5. The container or the method of any one of the preceding items, wherein the at least one access port is the same as or different from the overwrap access port.

Item 6. The container or the method of item 5, wherein at least one of the first access port and the overwrap access port includes a spike port.

Item 7. The container or the method of item 6, wherein the spike port includes a membrane.

Item 8. The container or the method of item 5, wherein at least one of the first access port and the overwrap access port includes a luer valve.

Item 9. The container or the method of item 8, wherein the luer valve includes an internal valve and a female luer end, wherein the internal valve is configured to open when a male luer fitting is attached to the female luer end, and wherein the internal valve is configured to close when the male luer fitting is detached from the female luer end.

Item 10. A container for cryopreserving a material in a sterile environment, wherein the material includes a biomaterial, and wherein the container includes: an inner bag, wherein the interior of the inner bag includes a sterile environment for storing the material; a spike port configured to provide fluid access to the interior of the inner bag; an inlet tube configured to provide fluid access to the interior of the inner bag; an overwrap bag, wherein the interior of the overwrap bag includes a sterile environment for storing the material and wherein the inner bag is enclosed within the interior of the overwrap bag; and an overwrap access port includes a spike port configured to provide fluid access to the interior of the overwrap bag; wherein each of the inner bag, the overwrap bag, the spike port, and the overwrap access port include fluoroethylenepropylene (FEP).

Item 11. The container, the method, or the container for cryopreserving a material in a sterile environment of any one of the preceding items, wherein at least one of the inner bag and the overwrap bag is transparent.

Item 12. The container, the method, or the container for cryopreserving a material in a sterile environment of any one of the preceding items, wherein the overwrap bag includes a label pocket configured to store a label.

Item 13. The container, the method, or the container for cryopreserving a material in a sterile environment of item 12, wherein the label pocket is configured to close by pinching, heat sealing, welding, dielectric sealing, radio-frequency welding, ultrasonic welding, stapling, taping, or any combination thereof.

Item 14. The container, the method, or the container for cryopreserving a material in a sterile environment of item 12, wherein the label pocket is configured to protect the label from smudging, defacing, tearing, deterioration, or any combination thereof.

Item 15. The container, the method, or the container for cryopreserving a material in a sterile environment of any one of the preceding items, wherein the at least one access port includes an inlet tube configured to transport the material into the inner bag in a sterile manner.

Item 16. The container, the method, or the container for cryopreserving a material in a sterile environment of item 15, wherein the inlet tube includes a sealable material.

Item 17. The container, the method, or the container for cryopreserving a material in a sterile environment of item 16, wherein the inlet tube includes a polymer, such as polyvinylchloride (PVC), fluoroethylenepropylene (FEP), a thermoplastic elastomer such as C-Flex®, or any combination thereof.

Item 18. The container, the method, or the container for cryopreserving a material in a sterile environment of item 15, wherein the inlet tube is configured to connect to an external source for transporting the material into the inner bag in a sterile manner.

Item 19. The container, the method, or the container for cryopreserving a material in a sterile environment of item 18, wherein the inlet tube is configured to close after the material is transported into the inner bag.

Item 20. The container, the method, or the container for cryopreserving a material in a sterile environment of item 19, wherein the inlet tube is configured to close by pinching, heat sealing, welding, dielectric sealing, radio-frequency welding, ultrasonic welding, stapling, taping, or any combination thereof.

Item 21. The container, the method, or the container for cryopreserving a material in a sterile environment of item 19, wherein the inlet tube is configured to disconnect in a sterile manner from the external source after the inlet tube is closed.

Item 22. The container, the method, or the container for cryopreserving a material in a sterile environment of item 15, wherein a portion of the overwrap bag is configured to close over at least a portion of the inlet tube.

Item 23. The container, the method, or the container for cryopreserving a material in a sterile environment of any of the preceding items, wherein the inner bag includes a cover configured to expose, by tearing, cutting, piercing, or any combination thereof, the at least one access port.

Item 24. The container, the method, or the container for cryopreserving a material in a sterile environment of any one of the preceding items, wherein the overwrap bag includes a secondary cover configured to expose, by tearing, cutting, piercing, or any combination thereof, the overwrap access port.

Item 25. The container, the method, or the container for cryopreserving a material in a sterile environment of any one of the preceding items, wherein the overwrap bag is configured to store a leak of the material from the interior of the inner bag.

Item 26. The container, the method, or the container for cryopreserving a material in a sterile environment of any one of the preceding items, wherein the container is inert to the material.

Item 27. The container, the method, or the container for cryopreserving a material in a sterile environment of any one of the preceding items, wherein the container is flexible and resistant to fracture to approximately −196° C.

Item 28. The container, the method, or the container for cryopreserving a material in a sterile environment of any one of the preceding items, wherein each of the inner bag, the overwrap bag, and the overwrap access port consists essentially of fluoroethylenepropylene (FEP).

Item 29. The method of item 3, wherein storing the material in the container further includes: connecting an external source to the at least one access port of the container, wherein the at least one access port includes an inlet tube; transporting the material in a sterile manner from the external source to the interior of the inner bag using the inlet tube; closing the inlet tube; and detaching the external source in a sterile manner from the inlet tube.

Item 30. The method of item 29, further including: closing the overwrap bag over the inlet tube.

Item 31. The method of item 3, further including: freezing the container.

Item 32. The method of item 31, wherein freezing the container further includes placing the container between two surfaces.

Item 33. The method of item 32, wherein the two surfaces cool the container at a rate between approximately 0.1° C. per minute and 10° C. per minute, such as at a rate of 1° C. per minute.

Item 34. The method of item 31, wherein freezing the container further includes placing the container in a liquid nitrogen bath.

Item 35. The method of item 3, further including: accessing the material stored in the container, wherein accessing the material further includes: exposing at least one of the at least one access port and the overwrap access port; and accessing the material through at least one of the at least one access port and the overwrap access port.

Item 36. The method of item 35, wherein accessing the material further includes piercing a membrane of at least one of the at least one access port and the overwrap access port.

Item 37. The method of item 35, wherein accessing the material further includes: removing the container from a cryopreservation system; and thawing the material.

Item 38. The method of item 37, wherein thawing the material includes placing the container in a water bath.

Item 39. The container, the method, or the container for cryopreserving a material in a sterile environment of any one of the preceding items, wherein the at least one access port is at least partially enclosed within the overwrap bag.

Item 40. The container, the method, or the container for cryopreserving a material in a sterile environment of any one of the preceding item, wherein the at least one access port is configured to provide sterile fluid access to the interior of the inner bag, and wherein the overwrap access port is configured to provide sterile fluid access to the interior of the overwrap bag.

The following example is provided to better disclose and teach processes and compositions of the present invention. It is for illustrative purposes only, and it must be acknowledged that minor variations and changes can be made without materially affecting the spirit and scope of the invention as recited in the claims that follow.

Example 1

A procedure for testing the container as described above includes testing the container for resistance to damage due to repeated freezing at approximately −196° C. in a liquid nitrogen bath. First, the container is filled with an appropriate volume of a testing material, such as beer or a tissue culture media that contains red dye. Beer is chosen for its high carbon dioxide content, which carbonation will be largely responsible for the expansion and contraction of the liquid in the container, and for its protein content, making it similar to a culture fluid. The filled container is connected to a strip of FEP, or other suitable material that will not be damaged by exposure to the liquid nitrogen, and is lowered into the liquid nitrogen bath. The container resides in the liquid nitrogen bath for ten minutes after the liquid nitrogen has ceased boiling, unless otherwise instructed.

The container is then removed from the liquid nitrogen bath and placed into a water bath with an initial temperature between approximately 20° C. and 40° C. The volume of the water bath can be much larger than the volume of the liquid nitrogen bath. The container and the testing material are permitted to thaw, after which the container is visually inspected for damage. This cycle of freezing and subsequently thawing the filled container can be repeated multiple times, and the container is inspected for damage, including any type of leak of the material from the inner and/or overwrap bags, after each thaw. The container can be left in the liquid nitrogen bath if time constraints require interruption of the cycle.

If the container has leaked any of the testing material into the outside environment (e.g., the liquid nitrogen bath or the water bath) during a freezing and thawing cycle, which would indicate a failure of both the inner bag and the overwrap bag, then the test is discontinued and the number of previous freeze and thaw cycles successfully survived by the filled container, if any, are noted. If the container exhibits no leakage of the testing material into the outside environment, the container and the testing material are returned to the liquid nitrogen bath to initiate another cycle of freezing and thawing the filled container. When ten successive cycles of freezing and thawing have been completed, the container is compared to other containers that have not been subjected to any freezing processes. Ten cycles are the maximum number of cycles to which the filled container is exposed, as ten consecutive cycles would be a maximal test of the viability of a biomaterial stored in the container.

Containers as described in the embodiments above are tested in accordance with this operating procedure. Different sizes of "F-series" containers that include FEP are tested, each with two different volumes of testing material. The testing material includes beer. Each container is exposed to multiple cycles of freezing and thawing and is visually inspected after each thaw for any type of leak into the outside environment that would signal a failure of both the inner bag and the overwrap bag and would compromise the sterility of the testing material. If the container does not maintain the sterility of the testing material (i.e., leaks the testing material into the outside environment during a freezing and thawing cycle), the container receives a "Fail" designation. If the container maintains the sterility of the testing material (i.e., prevents a leak of that material into the outside environment) after ten successive freezing and thawing cycles, the container receives a "Pass" designation. As indicated by the "Pass" designations shown below in Table 1, each of the containers withstood ten successive freezing and thawing cycles and maintained the sterility of the testing material.

TABLE 1

| Container | Volume of Testing Material | Pass or Fail |
| --- | --- | --- |
| Container 1: F-series Model 6F | 5.1 mL | Pass |
| Container 1: F-series Model 6F | 6.9 mL | Pass |
| Container 2: F-series Model 20F | 17 mL | Pass |
| Container 2: F-series Model 20F | 23 mL | Pass |
| Container 3: F-series Model 60F | 51 mL | Pass |
| Container 3: F-series Model 60F | 69 mL | Pass |
| Container 4: F-series Model 120F | 102 mL | Pass |
| Container 4: F-series Model 120F | 139 mL | Pass |
| Container 5: F-series Model 180F | 153 mL | Pass |
| Container 5: F-series Model 180F | 207 mL | Pass |

The container of the present invention represents a departure from and improvement over conventional cryopreservation containers. Cryopreservation processes are used to preserve biological materials because the materials must be frozen and stored at temperatures below −182° C. to arrest biologic degradation. These processes, including the freezing processes carried out at approximately −196° C. in liquid nitrogen baths and subsequent thawing processes carried out with warm water baths, routinely involve the thermal expansion of water and phase changes in substances including carbon dioxide, oxygen, and nitrogen. Conventional containers, including those made using plastics such as ethylvinylacetate, become brittle below −50° C. and are prone to fracture during freezing. Fractures in these conventional containers can lead to a leak of the biomaterial stored in the container, which can lead to loss of the biomaterial and contamination of the biomaterial, the container, and the environment in which the container is located. A leak can contaminate both the freezing environment (e.g., the liquid nitrogen bath) and the thawing environment (e.g., the warm water bath). Additionally, some conventional containers are created by filling a vessel, tube, or bag and then placing that bag into a separate bag and then closing the separate bag. However, the handling involved in placing the filled bag inside of the separate bag and closing the separate bag is inherently non-sterile and also does not provide a closed environment for the filled bag. In addition, such conventional containers lack any means for the sterile recovery of material that may leak from the filled bag into the separate bag during freezing or thawing of the container.

By contrast, the container of the present invention provides a user with the ability to both fill and empty the container in a sterile manner, regardless of whether the material has leaked into the overwrap bag due to possible damage to the inner bag. Any leaks of the material are contained within the interior of the overwrap bag, preventing loss of the material and a sterile, closed environment for the material. Both the inner bag and the overwrap bag can be accessed and sealed without compromising the sterility of the container or the environment in which the container is located. Further, each of the inner bag and overwrap bag can be transparent so as to observe any leakage of the material or damage to the container. Moreover, the container can include FEP, a material that remains flexible and resistant to fracture down to the freezing temperatures used in cryopreservation (e.g., −196° C.) and is also inert to all biomaterials. The use of FEP and similar materials also permits the container to be sterilized by conventional methods that do not degrade the FEP or similar materials. In an embodiment, the container can be sterilized by conventional autoclave or irradiation methods. In addition, the simple construction and durable materials of the container provide both economy of production and ease of sterilization, and the container is no more difficult to use than conventional intravenous bags, as it can employ conventional intravenous fittings for the access ports that are familiar to members of the medical and laboratory industries.

Certain features, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges includes each and every value within that range.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A container comprising:
   an inner bag, wherein the interior of the inner bag comprises a sterile environment for storing a material;
   at least one access port configured to provide fluid access to the interior of the inner bag;
   an overwrap bag, wherein the interior of the overwrap bag comprises a sterile environment for storing the material and wherein the inner bag is enclosed within the interior of the overwrap bag; and
   an overwrap access port configured to provide fluid access to the interior of the overwrap bag.

2. The container of claim 1, wherein the material comprises a biomaterial.

3. A method of preserving a material, wherein the material comprises a biomaterial, the method comprising:
   storing the material in a container, wherein the container comprises: an inner bag, wherein the interior of the inner bag comprises a sterile environment for storing the material; at least one access port configured to provide fluid access to the interior of the inner bag; an overwrap bag, wherein the interior of the overwrap bag comprises a sterile environment for storing the material and wherein the inner bag is enclosed within the interior of the overwrap bag; and an overwrap access port configured to provide fluid access to the interior of the overwrap bag.

4. The container of claim 1, wherein at least one of the inner bag, the overwrap bag, the at least one access port, and the overwrap access port comprises fluoroethylenepropylene (FEP).

5. The container of claim 1, wherein at least one of the first access port and the overwrap access port comprises a spike port.

6. The container of claim 1, wherein at least one of the first access port and the overwrap access port comprises a luer valve.

7. A container for cryopreserving a material in a sterile, closed environment, wherein the material comprises a biomaterial, and wherein the container comprises:
   an inner bag, wherein the interior of the inner bag comprises a sterile, closed environment for storing the material;
   a spike port configured to provide fluid access to the interior of the inner bag;
   an inlet tube configured to provide fluid access to the interior of the inner bag;
   an overwrap bag, wherein the interior of the overwrap bag comprises a sterile, closed environment for storing the material and wherein the inner bag is enclosed within the interior of the overwrap bag; and
   an overwrap access port comprising a spike port configured to provide fluid access to the interior of the overwrap bag;
   wherein each of the inner bag, the overwrap bag, the spike port, and the overwrap access port comprise fluoroethylenepropylene (FEP).

8. The container of claim 1, wherein the at least one access port comprises an inlet tube configured to transport the material into the inner bag in a sterile manner.

9. The container of claim 1, wherein the inner bag comprises a cover configured to expose the at least one access port.

10. The container of claim 1, wherein the overwrap bag comprises a secondary cover configured to expose the overwrap access port.

11. The container of claim 1, wherein the overwrap bag is configured to store a leak of the material from the interior of the inner bag.

12. The method of claim 3, wherein storing the material in the container further comprises:
    connecting an external source to the at least one access port of the container, wherein the at least one access port comprises an inlet tube;
    transporting the material in a sterile manner from the external source to the interior of the inner bag using the inlet tube;
    closing the inlet tube; and
    detaching the external source in a sterile manner from the inlet tube.

13. The method of claim 3, further comprising:
    accessing the material stored in the container, wherein accessing the material further comprises:
    exposing at least one of the at least one access port and the overwrap access port; and
    accessing the material through at least one of the at least one access port and the overwrap access port.

14. The container of claim 1, wherein the at least one access port is at least partially enclosed within the overwrap bag.

15. The container of claim 1, wherein the at least one access port is configured to provide sterile fluid access to the interior of the inner bag, and wherein the overwrap access port is configured to provide sterile fluid access to the interior of the overwrap bag.

16. The container of claim 1, wherein the container comprises at least one sterile, closed environment for storing the material.

* * * * *